United States Patent
Hu et al.

(10) Patent No.: US 9,981,912 B2
(45) Date of Patent: May 29, 2018

(54) COCRYSTAL OF LORCASERIN, PREPARATION METHODS, PHARMACEUTICAL COMPOSITIONS AND USES THEREOF

(71) Applicant: HANGZHOU PUSHAI PHARMACEUTICAL TECHNOLOGY CO., LTD., Hangzhou, Zhejiang (CN)

(72) Inventors: Chenyang Hu, Zhejiang (CN); Xiaoxia Sheng, Zhejiang (CN); Xiaohong Sheng, Zhejiang (CN); Qiang Jia, Zhejiang (CN)

(73) Assignee: HANGZHOU PUSHAI PHARMACEUTICAL TECHNOLOGY CO., LTD., Hangzhou (CN)

( * ) Notice: Subject to any disclaimer, the term of this patent is extended or adjusted under 35 U.S.C. 154(b) by 0 days. days.

(21) Appl. No.: 15/107,032

(22) PCT Filed: Mar. 27, 2015

(86) PCT No.: PCT/CN2015/075175
§ 371 (c)(1),
(2) Date: Jun. 21, 2016

(87) PCT Pub. No.: WO2015/161730
PCT Pub. Date: Oct. 29, 2015

(65) Prior Publication Data
US 2017/0327467 A1    Nov. 16, 2017

(30) Foreign Application Priority Data
Apr. 21, 2014 (CN) .......................... 2014 1 0159203

(51) Int. Cl.
*A61K 31/55* (2006.01)
*C07D 223/16* (2006.01)

(52) U.S. Cl.
CPC ........ *C07D 223/16* (2013.01); *C07B 2200/13* (2013.01)

(58) Field of Classification Search
CPC .............................. A61K 31/55; C07D 223/16
USPC ...................................... 514/217.01; 540/594
See application file for complete search history.

(56) References Cited

U.S. PATENT DOCUMENTS 6,953,787 B2    10/2005    Smith et al.

FOREIGN PATENT DOCUMENTS

| WO | WO 2005/019179 A2 | 3/2005 |
| WO | WO 2006/069363 A2 | 6/2006 |
| WO | WO 2012/030927 A2 | 3/2012 |
| WO | WO 2012/030951 A1 | 3/2012 |
| WO | WO 2012/030957 A2 | 3/2012 |

*Primary Examiner* — Brenda L Coleman
(74) *Attorney, Agent, or Firm* — Sterne, Kessler, Goldstein & Fox PLLC

(57) ABSTRACT

The present invention relates to a new type of eutectic crystal of lorcaserin hydrochloride and benzoic acid, when compared with the prior art, the eutectic crystal has the improved properties of good stability, low solubility, and being suitable for the application of controlled-release preparation; the present invention also relates to a method for preparing the eutectic crystal, a pharmaceutical composition thereof and the use thereof in the manufacture of drugs for treating and/or preventing diseases associated with $5HT_{2C}$.

17 Claims, 3 Drawing Sheets

COCRYSTAL OF LORCASERIN, PREPARATION METHODS, PHARMACEUTICAL COMPOSITIONS AND USES THEREOF

BACKGROUND OF THE INVENTION

Field of the Invention

The present invention relates to the technical field of crystallization in pharmaceutical chemistry. Specifically, the present invention relates to a novel cocrystal of lorcaserin, preparation methods, pharmaceutical compositions and uses thereof.

Background Art

During the preformulation stage, the solid form of a drug often needs to be chosen according to properties of the drug and requirements for the target formulations. Different solid forms of a drug may lead to different physical and chemical properties, such as stability, solubility, dissolution rate and hygroscopicity, which may further affect its efficacy, pharmacology and toxicology; Different solid forms of a drug may have different particle properties and powder properties, such as morphology, size, density and flowability, etc., which may affect processability and quality, even efficacy of formulations. Therefore, choosing solid forms of a drug is an important factor to be considered in formulation.

Solid forms of drugs mainly include polymorph, salt, hydrate, solvate and cocrystal. Pharmaceutical cocrystal is the crystalline form combined an active pharmaceutical ingredient (API) with cocrystal former(s) (CCF) in a fixed stoichiometric ratio by weak interactions, in which pure forms of components are solids at ambient temperature. The weak interaction is defined as neither ionic bond interaction nor covalent bond interaction including such as hydrogen bond, van der Waals forces, $\pi$-$\pi$ interactions and halogen bond. Cocrystal is a multi-component crystal, including binary cocrystal formed between two neutral solids and pluralistic cocrystal formed by neutral solid and salt or solvate.

Compared with traditional solid forms, such as polymorphs, salts, hydrates or solvates, etc., pharmaceutical cocrystals have greater advantages. For salts, salt formation is dependent on electrostatic attraction between API ions and acidic or alkali ions and is only applicable to ionizable drug; while intermolecular forces exist between API and CCF in cocrystal. For those non-dissociated and weakly dissociated drugs, it is an important means to change solid forms by forming cocrystals. For solvates, there are only a few kinds of pharmaceutically acceptable solvents at present. Especially, organic solvent molecules in solvates are easy to migrate in solids and have high vapor pressure, such solvates are prone to desolvation and convert to amorphous substances or recrystallization. CCFs in cocrystal seldom change physical status such as volatilization, sublimation or phase separation. Therefore, solvents in cocrystals are more stable than in solvates. With above advantages, cocrystals are a solid form with great potentials and have profound influence on pharmaceutical preformulation and formulation.

Lorcaserin is a novel weight-loss drug developed by Arena Pharmaceuticals. It is a selective 5-$HT_{2C}$ receptor agonist. 5-$HT_{2C}$ receptor is highly expressed in the central nervous system; the physiological effects thereof are related to generation of brain fluid, pathophysiology of anxiety, eating behavior and energy balance of the body. Lorcaserin can help obese patients to induce satiety, reduce food intake, and promote weight loss by modulating 5-$HT_{2C}$ receptor activity. U.S. Food and Drug Administration (FDA) approved lorcaserin on Jun. 27, 2012 with its trade name of Belviq. The Listed dosage form is oral immediate-release tablets containing lorcaserin hydrochloride hemihydrate, 10 mg strength. It is suitable for weight management in adults with a body mass index BMI≥30 or greater (obese) or BMI≥27 or greater (overweight) in the presence of at least one weight-related diseases (such as hypertension, hyperlipidemia or type 2 diabetes). Lorcaserin is also useful in the treatment or prevention of other central nervous system diseases mediated by 5-$HT_{2C}$.

The chemical name of lorcaserin is (R)-8-chloro-1-methyl-2,3,4,5-tetrahydro-1H-3-benzazepine, also known as APD356. Its chemical structural formula is as follows:

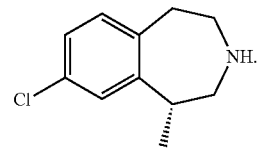

Patent document U.S. Pat. No. 6,953,787B2 disclosed racemic lorcaserin and its preparation method.

Patent document WO2005/019179A2 disclosed lorcaserin hydrochloride and lorcaserin L-(+)-tartrate.

Patent document WO2006/069363A2 disclosed a hemihydrate of lorcaserin hydrochloride (referred to as crystalline Form III in the present invention) and two anhydrous forms (crystalline Form I and crystalline Form II). It also disclosed that the crystalline Form III is the most stable form and has poor hygroscopicity.

Patent document WO2012/030927A2 disclosed various salts, hydrates or solvates of lorcaserin, such as hydriodate, maleate, fumarate, hemifumarate, orotate, orotate hydrate, trans-cinnamate, heminapadisilate, heminapadisilate solvate 1, heminapadisilate solvate 2, mandelate hydrate and hemipamoate, but the document did not provide details of these salts or solvates in the formulation applications.

Patent document WO2012/030951A1 disclosed lorcaserin salts, such as disulfate, hemisulphate, mesylate, hydrobromide, nitrate, adipate, malonate, hetnimalonate and glycollate. The patent document mentioned that the above lorcaserin salts had good water solubility and were suitable for preparation of immediate-release dosage forms.

Patent document WO2012/030957A2 disclosed lorcaserin salts such as phosphate, hemiedisylate, citrate, hemioxalate, succinate, oxoglutarate, and oxoglutarate solvate. The patent document mentioned that the above lorcaserin salts were stable to humidity and suitable for application in solid formulations.

In the prior art, researches of lorcaserin solid forms were focused on development and application of its salts, hydrates, solvates and their polymorphs, while the present invention relates to novel solid forms of lorcaserin to expand physical form types for formulation development. In addition, although immediate-release tablets of lorcaserin have advantageous properties including fast dissolution and reaching the effective plasma concentration quickly, there were still some disadvantages, such as variations in the plasma concentration and multiple doses per day. Therefore, there is still a need to develop new solid forms of lorcaserin.

BRIEF SUMMARY OF THE INVENTION

In view of the disadvantages in the prior art, the objective of the present invention is to provide a novel cocrystal of lorcaserin. Compared with the prior art, the cocrystal of lorcaserin has one or more improved properties, such as good stability, good solubility, fast dissolution, high crystallinity, low hygroscopicity, easy purification and treatment, high-purity, low residual solvent, good particle morphology, good processability such as flowability, powder plasticity, tapped density and compressibility, improved formulation, improved bioavailability and efficacy, and is suitable for application in new dosage forms such as sustained-release and controlled-release formulations. The present invention also relates to preparation methods of the cocrystal, pharmaceutical compositions and uses thereof.

As a novel pharmaceutical solid form, the development of pharmaceutical cocrystal is comparatively new. As it is impossible to predict which countermolecules may form a cocrystal or whether the obtained cocrystals would have improved physical and chemical properties, cocrystals are still largely prepared on a trial and error basis.

The inventors of present invention performed a large number of experiments and surprisingly discovered a cocrystal of lorcaserin with improved properties by trying different countermolecules and reaction conditions.

According to the objective of the present invention, the present invention provides a cocrystal of lorcaserin hydrochloride and benzoic acid (hereinafter referred to as "the cocrystal" in the present invention). The cocrystal is a compound formed by lorcaserin hydrochloride, benzoic acid and water in the molar ratio of 1:1:1. Its structural formula is shown below:

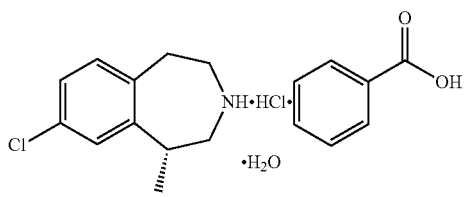

In one embodiment of the present invention, measured using Cu—Kα, radiation, the X-ray powder diffraction pattern of the cocrystal, expressed as 2θ angles, has the following characteristic peaks: 4.5±0.2°, 9.0±0.2°, 12.3±0.2°, 18.0±0.2°, 19.4±0.2° and 23.0±0.2°.

In one preferred embodiment of the present invention, the X-ray powder diffraction pattern of the cocrystal, expressed as 2θ angles, has the following characteristic peaks: 4.5±0.2°, 9.0±0.2°, 11.7±0.2°, 12.3±0.2°, 13.5±0.2°, 16.9±0.2°, 18.0±0.2°, 19.4±0.2°, 20.4±0.2°, 22.6±0.2°, 23.0±0.2° and 23.5±0.2°.

In the further preferred embodiment of the present invention, the X-ray powder diffraction pattern of the cocrystal, expressed as 2θ angles, has the following characteristic peaks with their relative intensities:

| Diffraction angel 2θ | Relative intensity % |
|---|---|
| 4.5 ± 0.2° | 7.3 |
| 9.0 ± 0.2° | 53.9 |
| 11.7 ± 0.2° | 6.0 |
| 12.3 ± 0.2° | 6.9 |
| 13.5 ± 0.2° | 6.7 |
| 16.9 ± 0.2° | 7.9 |
| 18.0 ± 0.2° | 22.9 |
| 18.2 ± 0.2° | 16.0 |
| 19.4 ± 0.2° | 18.9 |
| 20.4 ± 0.2° | 11.4 |
| 22.6 ± 0.2° | 58.1 |
| 23.0 ± 0.2° | 100.0 |
| 23.5 ± 0.2° | 38.1 |
| 24.1 ± 0.2° | 28.4 |
| 25.7 ± 0.2° | 13.0 |
| 26.8 ± 0.2° | 16.5 |
| 28.0 ± 0.2° | 9.1 |
| 29.4 ± 0.2° | 11.9 |
| 30.9 ± 0.2° | 7.5. |

Non-restrictively, in one specific embodiment of the present invention, the X-ray powder diffraction pattern of the cocrystal is shown in FIG. 2.

In one embodiment of the present invention, a single-crystal of the cocrystal was prepared. One of the preparation methods is, such as, evaporating an acetone solution of the cocrystal through a small hole to dryness at room temperature to obtain a single-crystal. As use herein, "evaporating an acetone solution of the cocrystal through a small hole" means the solution in the container is volatilized through a hole with a diameter of 2 mm for crystallization at the corresponding temperature.

Measured at the temperature of 100K, the single-crystal of the cocrystal has the following unit cell parameters: axial length a=6.1734(6) Å, b=7.6376(5) Å c=39233(4) Å; dihedral angle α=90°, β=90°, γ=90°; space group P 1 1 2$_1$. The cocrystal is a twin crystal consisting of two monoclinic systems, all the dihedral angles of the three unit vectors a, b, c are 90°.

In one embodiment of the present invention, the Fourier transform infrared spectrum of the cocrystal has characteristic peaks at wave numbers of 3384, 2971, 2861, 2524, 2362, 1700, 1595, 1315, 1270, 1119, 946, 818 and 710 cm$^{-1}$.

The solubility of the cocrystal in water is 8~9 mg/ml at 25° C., while the solubility of the known lorcaserin hydrochloride hemihydrate in water is more than 200 mg/ml at 25° C.

Compared with the known lorcaserin hydrochloride hemihydrate, the cocrystal in the present invention has the following advantageous properties:

(1) The solubility of the cocrystal in the present invention in water is 8~9 mg/ml which is more suitable for sustained-release formulation, as it can sustain therapeutic effects for a longer time, maintain a stable and effective plasma concentration, conform to clinical requirements, reduce dosing frequency, and significantly improve patients' compliance. Under the same prescription, the known lorcaserin hydrochloride hemihydrate may be quickly and completely released due to its high solubility, and cause a gap period during which the plasma concentration lower than the effective concentration.

(2) Compared with the coating-controlled sustained release formulations, the release rate of lorcaserin hydrochloride in the cocrystal formulation in the present invention is less dependent on coating due to its slower dissolution. It may avoid influences on the release rate caused by coating processes (such as coating thickness, coating continuity) and variations in different batches of coating materials.

(3) When placed at 25° C., 60% RH for 6 months, the cocrystal of the present invention remained its purity and crystalline form unchanged. When placed at 80° C. and 6000 lx light exposure for 10 days, decrease of the purity and increase of the maximum individual impurity content in the cocrystal were significantly lower than the corresponding data of the known lorcaserin hydrochloride hemihydrate. Therefore, the cocrystal of the present invention has good chemical stability and crystalline form stability; it is suitable for formulation requirements. It is less likely to have content uniformity, stability and formulation processability issues during pharmaceutical production and storage, thus reduce the risk of efficacy decrease and safety issue caused thereby and conducive to transport and storage.

According to the objective of the present invention, the present invention provides a preparation method of the cocrystal, which is selected from any one of the following methods, comprising:

(1) Forming a solution of benzoic acid in an organic solvent, wherein the organic solvent is selected from the group consisting of alcohols, ketones and esters; adding lorcaserin hydrochloride hemihydrates, the molar ratio of lorcaserin hydrochloride hemihydrate to benzoic acid is from 1:1~1.5:1, after the addition, stirring the mixture for crystallization, and obtaining the cocrystal.

Preferably, the organic solvent is selected from the group consisting of $C_1$ to $C_4$ alcohols, ethyl acetate and acetone, more preferably, the organic solvent is isopropanol;

Preferably, the concentration of the solution of benzoic acid in the organic solvent is from 75 to 120 mg/mL;

Preferably, the operation temperature of the preparation method is 10° C. to 40° C.; more preferably room temperature;

Preferably, the time of crystallization is 8 to 48 hours, more preferably 8 to 16 hours;

Preferably, lorcaserin hydrochloride hemihydrate is added in 2 to 6 equal parts, and stirred for 10 to 15 minutes after each addition.

(2) Forming a solution of lorcaserin hydrochloride hemihydrate in an organic solvent, wherein the organic solvent is selected from the group consisting of alcohols, ketones and esters; adding benzoic acid, the molar ratio of lorcaserin hydrochloride hemihydrate to benzoic acid is from 1:1~1:3, after the addition, stirring the mixture for crystallization, and obtaining the cocrystal;

Preferably, the organic solvent is selected from the group consisting of $C_1$ to $C_4$ alcohols, ethyl acetate and acetone, more preferably, the organic solvent is isopropanol;

Preferably, the molar ratio of lorcaserin hydrochloride hemihydrate to benzoic acid is from 1:1 to 1:1.5.

Preferably, the concentration of the solution of lorcaserin hydrochloride hemihydrate in the organic solvent is from 50 to 100 mg/mL;

Preferably, the operation temperature of the preparation method is from 10° C. to 40° C.; more preferably room temperature;

Preferably, the time of crystallization is from 8 to 48 hours, more preferably from 8 to 16 hours;

Preferably, benzoic acid is added in 2 to 6 equal parts, and stirred the mixture for 10 to 15 minutes after each addition.

(3) Forming a mixed system of lorcaserin, hydrochloric acid and benzoic acid in an organic solvent, wherein the organic solvent is selected from the group consisting of alcohols, ketones, esters and haloalkanes, the molar ratio of lorcaserin, hydrochloric acid and benzoic acid is from 1:1:1 to 1:2:3, stirring the mixed system for crystallization, and obtaining the cocrystal;

Preferably, the organic solvent is selected from the group consisting of $C_1$ to $C_4$ alcohols, ethyl acetate, acetone and dichloromethane; more preferably, the organic solvent is isopropanol;

Preferably, the molar ratio of lorcaserin, hydrochloric acid and benzoic acid is from 1:1:1 to 1:2:2;

Preferably, the weight volume ratio of lorcaserin to the organic solvent in the mixed system is from 100 mg:1 mL to 200 mg:1 mL;

Preferably, the operation temperature of the preparation method is from 10° C. to 40° C.; more preferably room temperature;

Preferably, the time of crystallization is from 10 to 24 hours;

The mentioned hydrochloric acid is the aqueous solution of hydrogen chloride, and its concentration range is 1~4 mol/L.

In the above preparation methods (1), (2) and (3), "$C_1$ to $C_4$ alcohols" include methanol, ethanol, n-propanol, isopropanol, n-butanol, 2-butanol and isobutanol.

In the above preparation methods (1), (2) and (3), separation and drying of the cocrystal is performed by routine methods in the field. Separation is performed using the methods such as filtration. The detailed operation of filtration is: place the sample to be separated on filter paper and filter under reduced pressure. Drying methods such as blast drying and drying under reduced pressure are used; Drying device is fume hood, blast oven or vacuum oven; Drying is performed under reduced pressure or not, preferably the pressure is less than 0.09 MPa. Drying temperature is 10-40° C., preferably room temperature; Drying time is 1-72 hours, preferably 1-10 hours, and more preferably 1-2 hours.

(4) Adding a solvent into a mixture of lorcaserin hydrochloride hemihydrate and benzoic acid in which lorcaserin hydrochloride hemihydrate has equal molar ratio to benzoic acid, after keeping the mixture wetted completely with the solvent, grinding to dryness, and obtaining the cocrystal, wherein the solvent is selected from the group consisting of water and organic solvents.

In the preparation method (4), the organic solvent refers to a pharmaceutically acceptable solvent that does not affect biological activities of active pharmaceutical ingredient and is capable of wetting the mixture thereof.

Preferably, the solvent in the preparation method (4) is selected from the group consisting of acetone, acetonitrile and water;

In the preparation method (4), the amount of the solvent is enough when it can wet the mixture completely.

Preferably, the weight volume ratio of the mixture to the solvent is 150 mg:1 mL to 240 mg:1 mL;

Preferably, the operation temperature of the preparation method (4) is 10° C. to 40° C.;

more preferably, room temperature.

The mentioned "grinding" may be performed by routine methods in the field, such as grinding the sample in a mortar.

In the above preparation methods of the present invention, stirring may be performed by routine methods in the field such as, magnetic stirring or mechanical stirring. The stirring speed is 50~1800 r/min, preferably 300~900 r/min.

In the present invention, the preparation methods of the cocrystal are simple and easy to operate.

In the present invention, room temperature refers to 10-30° C.

In the present invention, lorcaserin can be prepared by referencing the methods described in examples 1-5 of patent document WO2005/019179A2. Lorcaserin hydrochloride hemihydrate (crystalline Form III) can be prepared by referencing the methods described in example 1 and example 2 of patent document WO2006/069363A2.

In the present invention, the crystalline form of the cocrystal is confirmed by X-ray powder diffraction pattern, and the structure of the cocrystal is confirmed by single-crystal X-ray diffraction. It is known to those skilled in the field that experimental errors of X-ray powder diffraction patterns depend on instrument conditions, sample preparations and sample purity. X-ray powder diffraction patterns may change with the change of instrument conditions. The relative intensities of peaks may change with the change of experimental conditions; therefore, the order of peak intensities should not be regarded as the only or the determining factor. Experimental errors of peak position should also be considered and generally the allowed errors are ±0.2°. Due to the effect of experimental factors including sample height, peak position may shift; generally, a small amount of peak shifting is acceptable experimental error. Hence, it is easily understood for those skilled in the field that any adducts from lorcaserin hydrochloride and benzoic acid having the same or similar X-ray powder diffraction pattern as that of the crystalline form in the present invention should be within the scope of the present invention.

The cocrystal in the present invention is pure and substantially free of any other crystals, crystalline forms and amorphous forms. "Substantially free of" means less than 20% (weight) of other crystals, crystalline forms, amorphous forms; preferably less than 10% (weight), more preferably less than 5% (weight), and most preferably less than 1% (weight).

The present inventors have also found in their researches that cocrystal formers are not limited to benzoic acid, and also include malonic acid, succinic acid, maleic acid, fumaric acid, citric acid, malic acid, tartaric acid, adipic acid, benzoic acid, p-aminobenzoic acid, fructose, aspartame, benzyl alcohol, sorbitol, dextrin, maltodextrin, saccharin, nicotinamide, urea, 2-aminopyrimidine, etc.

According to the objective of the present invention, the present invention provides a pharmaceutical composition, which comprises a therapeutically and/or preventively effective amount of active pharmaceutical ingredient selected from the cocrystal of lorcaserin hydrochloride and benzoic acid of the present invention or the cocrystal prepared by preparation methods of the present invention, and at least one pharmaceutically acceptable carrier or additive. The pharmaceutical composition comprises the cocrystal of lorcaserin hydrochloride and benzoic acid of the present invention in an amount of about 1% to 99% by weight, and at least one pharmaceutically acceptable carrier or additive in an amount of about 99% to 1% by weight. Moreover, the pharmaceutical composition may also comprise other acceptable pharmaceutical salts, solvates or hydrates of lorcaserin in their crystalline forms, amorphous forms or cocrystals. Optionally, the pharmaceutical composition may also contain one or more other active pharmaceutical ingredient(s).

The pharmaceutical compositions may be prepared as solid, semi-solid or liquid dosage forms. Solid oral dosage forms, include tablets, capsules, granules, pills and powders; liquid oral dosage forms, include solution, syrups, suspensions, dispersants and emulsions; injectable formulations, include solutions, dispersants and lyophilized powders which can be reconstituted to form a solution. The formulation may be suitable for immediate-release, sustained-release or controlled-release of the active ingredient. The formulation may be a regular, dispersible, chewable, orally soluble or rapidly dissolving form. Administrative routes of pharmaceutical compositions include oral administration, intravenous injection and subcutaneous injection, injection into tissue, transdermal administration, rectal administration, nasal dripping, etc. In order to maintain the cocrystal form of the present invention, solid oral dosage forms are preferred, including tablets, capsules, granules, pills and powders; more preferably sustained-release or controlled-release solid oral dosage forms.

In the cases of solid dosage forms, the pharmaceutically acceptable carriers or additives in the present invention include but are not limited to: diluents, e.g. starch, pregelatinized starch, lactose, powdered cellulose, microcrystalline cellulose, calcium hydrogen phosphate, tricalcium phosphate, mannitol, sorbitol, and sugar, etc.; adhesives, e.g. Arabia gum, guar gum, gelatin, polyvinylpyrrolidone, hydroxypropyl cellulose, hydroxypropyl methylcellulose, and polyethylene glycol, etc.; disintegrants, e.g. starch, sodium starch glycolate, pregelatinized starch, cross-linked polyvinyl polypyrrolidone, cross-linked sodium carboxymethylcellulose, and colloidal silica dioxide, etc.; lubricants, e.g. stearic acid, magnesium stearate, zinc stearate, sodium benzoate, and sodium acetate, etc.; glidants, e.g. colloidal silica dioxide; complex forming agents, e.g. cyclodextrin and resins of various grades; release rate controllers, e.g. hydroxypropyl cellulose, carboxymethyl cellulose, hydroxypropyl methyl cellulose, ethyl cellulose, methyl cellulose, methyl methacrylate, and wax, etc. Other pharmaceutically acceptable carriers or additives include but are not limited to film forming agents, plasticizers, coloring agents, flavoring agents, viscosity regulators, preservatives, and antioxidants, etc.

The pharmaceutical composition may be prepared by the method commonly known to those skilled in the art. In preparation of the pharmaceutical composition, the cocrystal of lorcaserin hydrochloride and benzoic acid in the present invention is mixed with one or more pharmaceutically acceptable carriers or additives, optionally with one or more other active ingredients. Solid formulations may be prepared by direct mixing, granulation and other processes.

According to the objective of the present invention, the present invention provides use of the cocrystal of lorcaserin hydrochloride and benzoic acid in the present invention in the manufacture of medicament for treating and/or preventing the diseases associated with $5HT_{2C}$.

According to the objective of the present invention, the present invention provides a method for treating and/or preventing the diseases associated with $5HT_{2C}$, which comprises administering to patients in need thereof a therapeutically and/or preventatively effective amount of the cocrystal of lorcaserin hydrochloride and benzoic acid in the present invention, or the cocrystal of lorcaserin hydrochloride and benzoic acid prepared by preparation methods of the present invention or the above pharmaceutical composition of the present invention. The patients refer to mammals, including humans. In some embodiments of the present invention, the dose is from about 0.01 to 100 mg/kg/day, a convenient daily dose that is easy to use. The dose is adjusted according to the type and severity of disease, general health condition of the patient, the characteristics of the formulation and the route of administration, etc.

The diseases associated with $5HT_{2C}$ mentioned above include but are not limited to obesity, central nervous system diseases, central nervous system injury, cardiovascular diseases, gastrointestinal disorders, diabetes insipidus, sleep apnea, depression, atypical depression, bipolar disorder, anxiety disorders, obsessive compulsive disorder, social phobia or panic state, sleep disorders, sexual dysfunction, psychoses, schizophrenia, migraine and symptoms associated with head pain or other pain, increased intracranial pressure, epilepsy, personality disorders, age-related behavioral disorders, behavioral disorders associated with dementia, organic mental disorders, childhood mental disorders, aggression, age-related memory disorders, chronic fatigue syndrome, drug and alcohol addiction, bulimia, anorexia nervosa or premenstrual tension.

EXAMPLES

Figure 1:
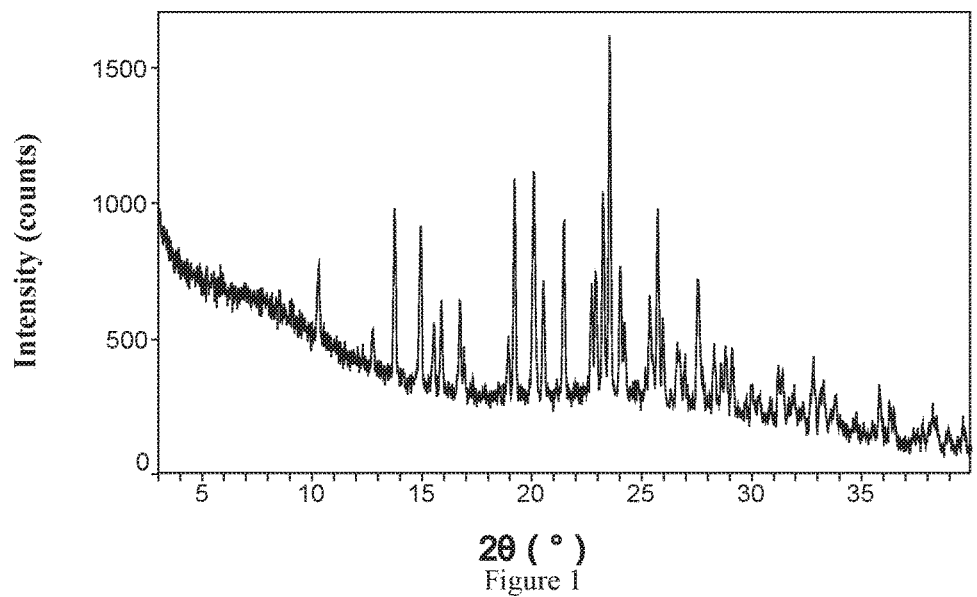
FIG. 1 is the XRPD pattern of the crystalline Form III of lorcaserin hydrochloride hemihydrate prepared according to preparation example 1.

The present invention refers further to the following examples. Those examples describe the cocrystal of the present invention, its preparations and applications in detail. It will be apparent to those skilled in the art that various modifications can be made to materials and methods without departing from the scope of the present invention.

Instruments and Characterization Methods:

X-ray powder diffraction (XRPD): performed on Bruker D8 Advance diffractometer equipped with θ-2θ goniometer, Mo monochrotneter and Lynxeye detector by using Cu—Kα X-rays with the wavelength 1.54 nm at 40 kV and 40 mA. Before testing, the instrument is performance checked using corundum. The collection software is Diffrac Plus XRPD Commander. Place the testing sample on a non-reflective plate at room temperature. The detailed testing conditions: 2θ scan range, 3-40°, step size, 0.02°, speed, 0.2 s/step.

Single-crystal diffractometer: Eos CCD detector, four-circle Kappa tester, enhanced Mo and enhanced Cu light sources. Detection parameters: ambient temperature 100K, enhanced Cu light source, graphite monochromator, the wavelength 1.54 Å. Data analysis software is CrysAlisPro. The data was further analyzed by Shelxtl software, and then the molecular structure diagram can be obtained.

Infrared spectrometry (IR) data are collected on Bruker Tensor 27 equipped with an attenuated total reflection (ATR). OPUS is used both for instrument control software and data analysis software. Usually, the infrared spectra are collected over 600-4000 $cm^{-1}$. Both samples and the blank background are scanned for 16 s. The instrument resolution is 4 $cm^{-1}$.

$^1$H Nuclear magnetic resonance spectrum ($^1$H-NMR) data are collected on Bruker Ascene™ 500. Usually, the $^1$H-NMR spectra are collected using full-frequency excitation, spectral width 30 ppm, mono pulse, 30° angle excitation, scanning 16 times, digital quadrature detection, and temperature 298K.

High performance liquid chromatography (HPLC) data are collected on Waters 2695 under the following conditions: column, VP-ODS 150×4.6 mm, 5 μm; column temperature, 2.5° C.; injection volume, 5 μL; flow rate, 1.0 mL/min, mobile phase A is 0.05% trifluoroacetic acid aqueous solution, mobile phase B is acetonitrile, gradient elution of mobile phases is shown in table 1. Absorption spectra are recorded on UV-visible spectrophotometer at the detection wavelength of 220 nm.

TABLE 1

Gradient elution of mobile phases in HPLC

| Time (min) | Mobile phase A (%) | Mobile phase B (%) |
|---|---|---|
| 0 | 90 | 10 |
| 8 | 20 | 80 |
| 13 | 20 | 80 |
| 13.1 | 90 | 10 |
| 15 | 90 | 10 |

Unless particularly specified, all examples were conducted at room temperature.

Unless particularly specified, all reagents used in the examples were commercially purchased.

"Overnight" in the examples means that the experiment step took place over the night time, such as from 8 to 22 hours or from 10 to 18 hours, usually 16 hours.

Preparation Example 1

Lorcaserin hydrochloride hemihydrate (crystalline Form III) was prepared by referencing the processes described in example 1 and example 2 of WO2006/069363A2. The operating procedures are detailed as follows:

To 220 g of lorcaserin, 3 L of dichloromethane was added, and then 1.74 L 1 mol/L solution of HCl in ether was added, the mixture was stirred for 2 hours at room temperature. The solvent was removed by rotary evaporation, and 190 g of lorcaserin hydrochloride was obtained.

To 16 g of lorcaserin hydrochloride, 36 g of isopropanol was added, the mixture was heated to 60° C. to obtain a clear solution. To the solution 96 g of cyclohexane was added followed by 12.4 g of water, then the system was cooled to 20° C. in 2 hours with slow stirring. After solids were observed, the suspension was cooled to 0° C. and stirred for 3 hours at 0° C. The suspension was filtered and the filter cake was washed with 16 g of cyclohexane. Dried at 40° C. under vacuum, 15 of lorcaserin hydrochloride hemihydrate was obtained as white crystalline solids.

The $^1$H-NMR(CDCl$_3$) data is shown below: 10.2 (br s, 1H), 9.8 (br s, 1H), 7.14 (dd, 1H, J=2, 8 Hz), 7.11 (d, 1H, J=2 Hz), 7.03 (d, 1H, J=8 Hz), 3.6 (m, 2H), 3.5 (m, 2H), 2.8-3.0 (m, 3H), 1.5 (d, 3H. J=7 Hz).

The X-ray powder diffraction pattern was shown in FIG. 1, indicating that its crystalline form is the same as the crystalline Form III in the prior art disclosed in WO2006/069363A2.

Example 1

To the mixture of 160 mg of lorcaserin hydrochloride hemihydrate and 80 mg of benzoic acid, 1 mL of acetone was added. Kept the mixture completely wetted with acetone, then ground it to dryness to obtain 234 mg of the cocrystal, the molar yield was 94.7%.

Figure 2:
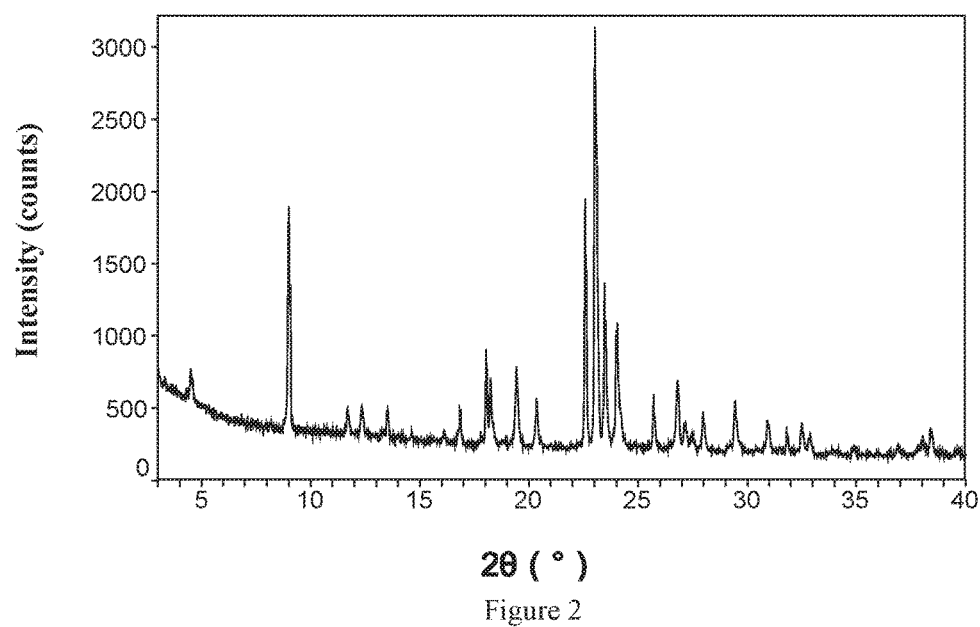
FIG. 2 is the XRPD pattern of the cocrystal in the present invention.

The XRPD pattern of cocrystal was shown in FIG. 2, indicating it is a crystalline substance.

Figure 4:
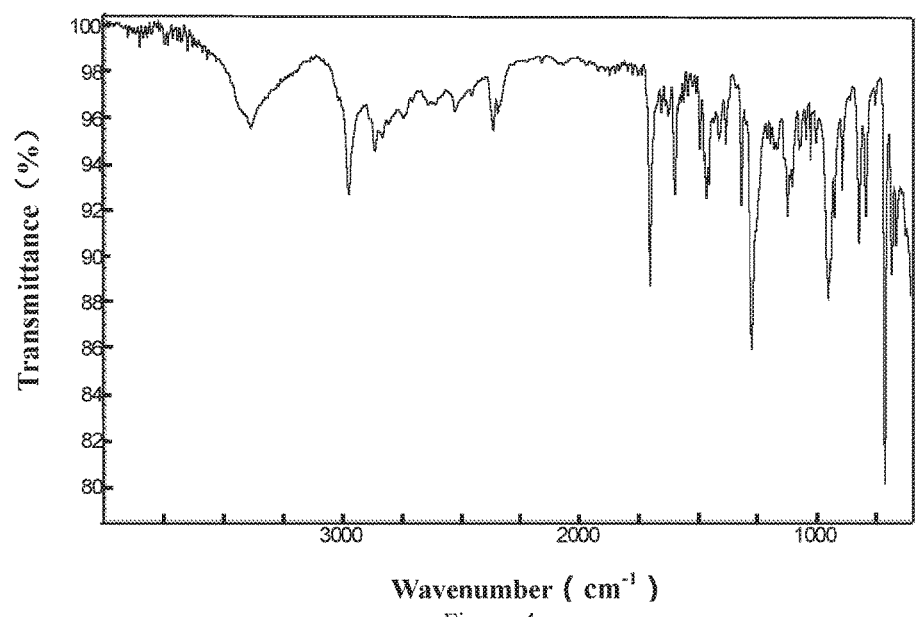
FIG. 4 is the IR spectrum of the cocrystal in the present invention.

The IR spectrum of the cocrystal was shown in FIG. 4, indicating that it has characteristic peaks at the wave numbers of 3384, 2971, 2861, 2524, 2362, 1700, 1595, 1315, 1270, 1119, 946, 818 and 710 $cm^{-1}$.

Example 2

Formed an acetone solution of the cocrystal prepared in Example 1, the acetone solution was injected into a 5 ml glass vial at room temperature, covered to seal the vial, then opened a small hole about 1 mm diameter in the cap for volatilization, the solution was volatilized to dryness, and the single-crystal for detection was obtained.

The single-crystal's lattice parameters were shown in Table 2.

TABLE 2

The single-crystal lattice parameters of the cocrystal
Lattice parameters

| | |
|---|---|
| Structural formula | Lorcaserin-HCl—H$_2$O—ArCOOH |
| molecular formula | C$_{18}$H$_{23}$Cl$_2$NO$_3$ |
| molecular weight (g/mol) | 372.29 |
| Crystal system | monoclinic system |
| Space groups | P 1 1 2$_1$ |
| Temperature/K | 100 |
| a/Å | 6.1734(6) |
| b/Å | 7.6376(5) |
| c/Å | 39.233(4) |
| α/° | 90.00 |
| β/° | 90.00 |
| γ/° | 90.00 |
| Z | 4 |
| V/Å$^3$ | 1849.83(30) |
| D$_{calc}$/g cm$^{-3}$ | 1.33662 |

In table 2, a, b, and c represent axial lengths of the unit cell, α, β, and γ represent dihedral angles, Z represents the number of molecules of Lorcaserin-HCl—H$_2$O—ArCOOH (Ar represents a phenyl group) in each unit cell, V represents cell volume, D$_{calc}$ represents cell density.

Single-crystal analytical parameters: residual factor R1=0.0442, weighted R value wR2=0.1194, goodness of fit GooF (S)=1.040. When R1 value is less than 0.05, wR2 value is less than 0.15, S value is almost 1; it indicates that the single-crystal data is reasonable.

Figure 3:
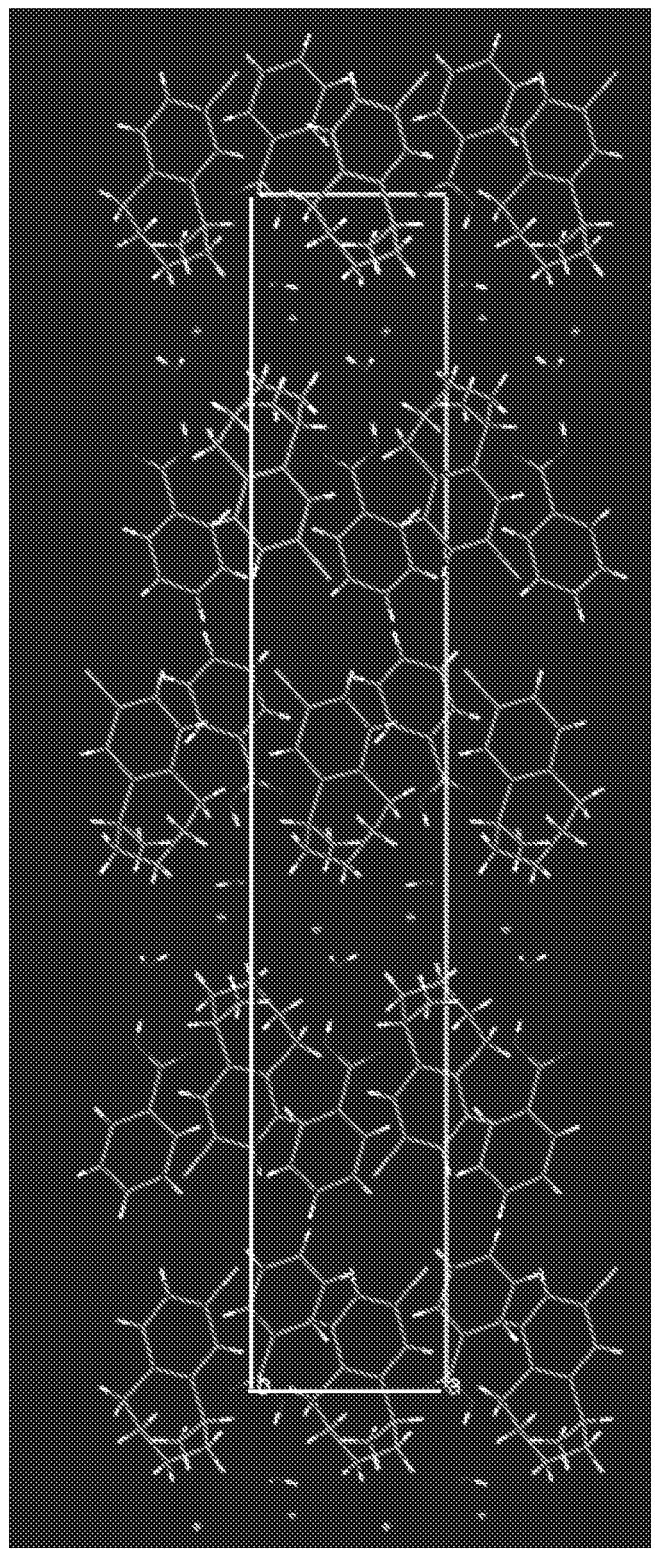
FIG. 3 is the molecular structure diagram of the cocrystal in the present invention.

Molecular structure diagram of the monocrystal is shown in FIG. 3, indicating that one cocrystal molecule consists of one lorcaserin molecule, one hydrogen chloride molecule, one benzoic acid molecule and one water molecule.

Figure 5:
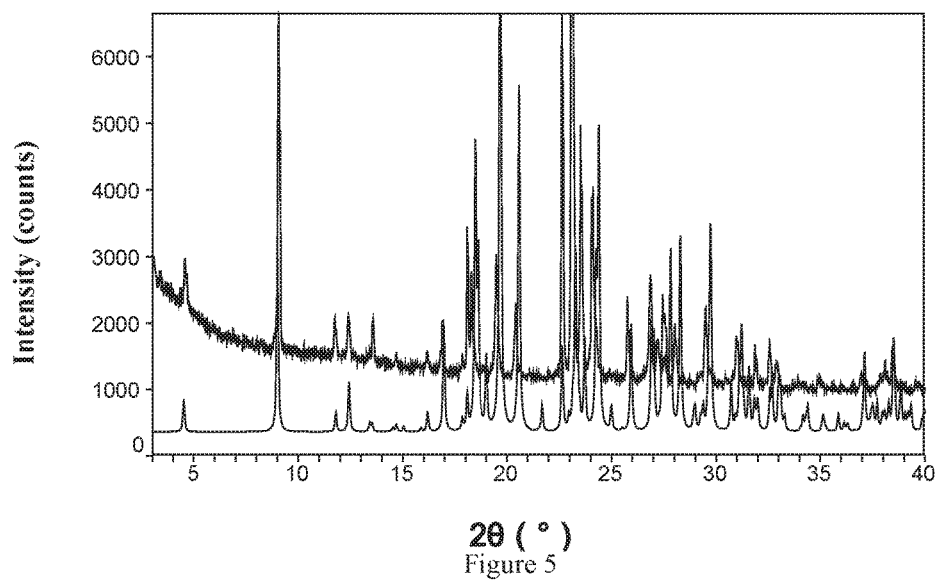
FIG. 5 is the XRPD pattern of the cocrystal in the present invention (top) and the simulated XRD pattern from single-crystal data (bottom).

The XRPD comparison diagram shown in FIG. 5 contains the simulated XRD patterns based on single-crystal dada (bottom) and the actual measured XRPD pattern of the cocrystal (top), showing that both are essentially identical.

Example 3

To the mixture of 100 mg of lorcaserin hydrochloride hemihydrate and 50 mg of benzoic acid, 1 mL of acetonitrile was added. Kept the mixture completely wetted with acetonitrile at 40° C., then ground it to dryness to obtain 136 mg of the cocrystal, the molar yield was 88.1%.

Example 4

To the mixture of 100 mg of lorcaserin hydrochloride hemihydrate and 50 mg of benzoic acid, 1 mL of water was added. Kept the mixture completely wetted with water at 40° C., then ground it to dryness to obtain 136 mg of the cocrystal, the molar yield was 70.0%.

Example 5

To 120 mg of benzoic acid, 1 mL of methanol was added to produce a methanol solution of benzoic acid by sonication. 240 mg of lorcaserin hydrochloride hemihydrate was equally divided into 6 parts with each part of 40 mg, and then the parts were added into the methanol solution of benzoic acid, respectively. After each addition, the mixture was stirred for 10~15 minutes. After the adding step, the mixture was stirred at room temperature for 8 hours, filtered, dried at room temperature for 1 hour, 55 mg of the cocrystal was obtained; the molar yield was 15.0%.

Example 6

To 240 mg of benzoic acid, 2 mL of n-butanol was added to produce a n-butanol solution of benzoic acid by sonication. 480 mg of lorcaserin hydrochloride hemihydrate was equally divided into 4 parts with each part of 120 mg, and then the parts were added into the n-butanol solution of benzoic acid, respectively. After each addition, the mixture was stirred for 10~15 minutes. After the additions, the mixture was stirred at room temperature for 8 hours, filtered, dried at room temperature for 1 hour, 120 mg of the cocrystal was obtained, and the molar yield was 16.4%.

Example 7

To 1.2 g of benzoic acid, 10 mL of isopropanol was added to produce an isopropanol solution of benzoic acid by sonication. 2.4 g of lorcaserin hydrochloride hemihydrate was divided into 6 parts in average with each part of 0.4 g, and then the parts were added into the isopropanol solution of benzoic acid, respectively. After each addition, the mixture was stirred for 10~15 minutes. After the additions, the mixture was stirred overnight at room temperature, filtered, dried at 40° C. for 2 hours, 1.63 g of the cocrystal was obtained, the molar yield was 44.6%.

Example 8

To 450 mg of benzoic acid, 4 mL of ethyl acetate was added to produce an ethyl acetate solution of benzoic acid by sonication at 40° C. 1.35 g of lorcaserin hydrochloride hemihydrate was equally divided into 6 parts, each part of 225 mg, and then the parts were added into the ethyl acetate solution of benzoic acid, respectively. After each addition, the mixture was stirred for 10~15 minutes. After the additions, the mixture was stirred for 48 hours, filtered, dried at 10° C. for 10 hours, 226 mg of the cocrystal was obtained, the molar yield was 16.5%.

Example 9

To 300 mg of benzoic acid, 4 mL of acetone was added to produce an acetone solution of benzoic acid by sonication, 900 mg of lorcaserin hydrochloride hemihydrate was equally divided into 2 parts with each part of 450 mg, and then the parts were added into the acetone solution of benzoic acid, respectively. After each addition, the mixture was stirred for 10~15 minutes. After the additions, the mixture was stirred at room temperature for 8 hours, filtered, dried at room temperature for 1 hour, 140 mg of the cocrystal was obtained; the molar yield was 15.3%.

Example 10

To 250 mg of lorcaserin hydrochloride hemihydrate, 5 mL of acetone was added to produce an acetone solution of lorcaserin hydrochloride hemihydrate by sonication. 375 mg of benzoic acid was equally divided into 3 parts with each part of 125 mg, then, the parts were added into the acetone solution of Lorcaserin hydrochloride hemihydrate, respectively. After each addition, the mixture was stirred for 10~15 minutes. After the additions, the mixture was stirred at room temperature for 8 hours, filtered, dried at room temperature for 2 hours, 48 mg of the cocrystal was obtained; the molar yield was 12.4%.

Example 11

To 200 mg of lorcaserin hydrochloride hemihydrate, 3 mL of ethyl acetate was added to produce an ethyl acetate solution of lorcaserin hydrochloride hemihydrate by sonication at 40° C. 300 mg of benzoic acid was equally divided into 2 parts with each part of 150 mg, then, the parts were added into the ethyl acetate solution of lorcaserin hydrochloride hemihydrate, respectively. After each addition, the mixture was stirred for 10~15 minutes. After the additions, the mixture was stirred overnight at room temperature, filtered, dried at 10° C. for 10 hours, 47 mg of the cocrystal was obtained, the molar yield was 15.2%.

Example 12

To 200 mg of lorcaserin hydrochloride hemihydrate, 4 mL of isopropanol was added to produce an isopropanol solution of lorcaserin hydrochloride hemihydrate by sonication. 100 mg of benzoic acid was equally divided into 2 parts with each part of 50 mg, then, the parts were added into the isopropanol solution of lorcaserin hydrochloride hemihydrate, respectively. After each addition, the mixture was stirred for 10~15 minutes. After the additions, the mixture was stirred overnight at room temperature, filtered, dried at 10° C. for 10 hours, 134 mg of the cocrystal was obtained, the molar yield was 43.4%.

Example 13

To 200 mg of lorcaserin hydrochloride hemihydrate, 2 mL of methanol was added to produce a methanol solution of lorcaserin hydrochloride hemihydrate by sonication at 40° C. 150 mg of benzoic acid was equally divided into 3 parts with each part of 50 mg, then, the parts were added into the methanol solution of lorcaserin hydrochloride hemihydrate, respectively. After each addition, the mixture was stirred for 10~15 minutes. After the additions, the mixture was stirred for 48 hours, cooled to room temperature, filtered, dried at 40° C. for 1 hour, 42 mg of the cocrystal was obtained, the molar yield was 13.6%.

Example 14

To 200 mg of lorcaserin hydrochloride hemihydrate, 2 mL of n-butanol was added to produce an n-butanol solution of lorcaserin hydrochloride hemihydrate by sonication. 300 mg of benzoic acid was equally divided into 6 parts with each part of 50 mg; the parts were added into the n-butanol solution of Lorcaserin hydrochloride hemihydrate, respectively. After each addition, the mixture was stirred for 10~15 minutes. After the additions, the mixture was stirred for 48 hours, cooled to room temperature, filtered, dried at 40° C. for 1 hour, 45 mg of the cocrystal was obtained, the molar yield was 14.6%.

Example 15

To 200 mg of lorcaserin, 1.02 mL of 1 mol/L HCl and 124 mg of benzoic acid, 1 mL of isopropanol was added to form a mixed system, the mixed system was stirred overnight, filtered, dried at 40° C. for 1 hour, 87 mg of the cocrystal was obtained, the molar yield was 23.0%.

Example 16

To 200 mg of lorcaserin, 1.02 mL of 1 mol/L HCl and 248 mg of benzoic acid, 1 mL of n-butanol was added to form a mixed system, the mixed system was stirred for 24 hours, filtered, dried at 40° C. for 4 hours, 62 mg of the cocrystal was obtained, the molar yield was 16.4%.

Example 17

To 200 mg of lorcaserin, 1.02 mL of 1 mol/L HCl and 248 mg of benzoic acid, 2 mL of ethanol was added to form a mixed system, the mixed system was stirred for 20 hours, filtered, dried at 40° C. for 4 hours, 65 mg of the cocrystal was obtained, the molar yield was 17.2%.

Example 18

To 200 mg of lorcaserin, 0.51 mL of 4 mol/L HCl and 248 mg of benzoic acid, 2 mL of ethyl acetate was added to form a mixed system, the mixed system was stirred for 20 hours, filtered, dried at 40° C. for 2 hours, 65 mg of the cocrystal was obtained, the molar yield was 17.2%.

Example 19

To 200 mg of lorcaserin, 1.02 mL of 1 mol/L HCl and 372 mg of benzoic acid, 1 mL of acetone was added to form a mixed system, the mixed system was stirred for 10 hours, filtered, dried at 40° C. for 2 hours, 48 mg of the cocrystal was obtained, the molar yield was 12.7%.

Example 20

To 200 mg of lorcaserin, 1.02 mL of 1 mol/L HCl and 372 mg of benzoic acid, 2 mL of dichloromethane was added to form a mixed system, the mixed system was stirred for 24 hours, filtered, dried at 40° C. for 1 hours, 54 mg of the cocrystal was obtained, the molar yield was 14.3%.

XRPD patterns and IR patterns (not shown) of the samples prepared in Examples 3~20 were the same as or similar to those of the sample cocrystal prepared in Example 1, indicating the crystalline forms obtained in examples 3~20 were the same as that of Example 1.

Test Example 1

Compared with lorcaserin hydrochloride hemihydrate prepared in the preparation example 1, the solubility of the cocrystal in the present invention was tested.

The operating procedures were detailed as follows:

Respectively, take 10 mg of the known lorcaserin hydrochloride hemihydrate or the cocrystal in the present invention as the sample, pure water was gradually added into each sample at 25° C. until the sample was completely dissolved, then solubility of the sample was calculated according to weights of the sample and water. The results were shown in Table 3.

TABLE 3

Results of the solubility

| Samples | Solubility (mg/mL) |
|---|---|
| Cocrystal (the present invention) | 8~9 mg/ml |
| Lorcaserin hydrochloride hemihydrate (the known) | >200 mg/ml |

The results of the solubility in Table 3 showed the solubility of the cocrystal in the present invention (8~9 mg/ml) is obviously lower than that of the known lorcaserin hydrochloride hemihydrate (>200 mg/ml), indicating that the cocrystal in the present invention is more suitable for preparing sustained-release formulations.

Test Example 2

Compared with tablets of lorcaserin hydrochloride hemihydrate prepared in the preparation example 1, tablets of the cocrystal in the present invention were prepared, tablet formulas were shown in Table 4; dissolution rate of the tables were tested.

TABLE 4

Tablet Formulas

|  | Starting materials | Prescription No. 1 (mg/tablet) | Prescription No. 2 (mg/tablet) |
|---|---|---|---|
| Core | Crystalline Form III (the known) | 25 | — |
|  | Cocrystal (the present invention) | — | 39 |
|  | Mannitol | 81.2 | 74.2 |
|  | HPMC K4M | 180 | 180 |
|  | Avicel PH102 | 72 | 65 |
|  | Magnesium stearate | 1.8 | 1.8 |
|  | Total of core | 360 | 360 |
| Coating | Surelease ®/Opadry ®75/25 | 18 | 18 |
| Total |  | 378 | 378 |

Note:
API is equivalent to 20 mg of lorcaserin hydrochloride free base.

The tablets were prepared by the following procedures: based on formulas of Table 4, prescribed API (either the known crystalline Form III or the cocrystal in the present invention), mannitol, HPMC K4M and Avicel PH102 were well mixed, magnesium stearate was added and mixed well; and then the mixture was compressed into tablet cores in a tablet machine. The tablet cores were coated by 5% weight in a coating machine, the coating liquid was Surelease®/Opadry® 75/25 with 12% (w/v) of solid content.

The dissolution test of tablets was conducted according to USP dissolution test apparatus I (basket method) in 900 mL of 0.1N HCl solution at 37° C. and the stirring rate of 100 rpm. Samples were withdrawn at 1 hour, 2 hours, 3 hours, 4 hours, 6 hours, 8 hours, 10 hours, 12 hours and 14 hours, the concentration of the dissolution liquid of tablets was determined by HPLC, the cumulative release percentage was calculated. The results were shown in Table 5.

TABLE 5

Cumulative release percentage of tablets

| Time (hours) | Formulation No. 1 (the known lorcaserin hydrochloride hemihydrate crystalline Form III) | Formulation No. 2 (the cocrystal in the present invention) |
|---|---|---|
| 1 | 10.2 | 3.5 |
| 2 | 26.1 | 13.8 |
| 3 | 38.7 | 17.6 |
| 4 | 50.5 | 37.7 |
| 6 | 66.8 | 56.4 |
| 8 | 80.2 | 70.2 |
| 10 | 89.1 | 82.8 |
| 12 | 93.6 | 90.1 |
| 14 | 97.5 | 95.7 |

The results shown in Table 5 indicated that, under the same formulation, the release rate of tablets of the known lorcaserin hydrochloride hemihydrates in pH=1.0 aqueous hydrochloric acid was faster than that of the cocrystal in the present invention, so the cocrystal in the present invention is more suitable for preparing sustained-release formulations. On the other hand, compared with the coating-controlled release rate, the release rate of the cocrystal formulation in the present invention has less dependence on the coating due to its own slower dissolution, so that influences on the release rate caused by coating processes (such as coating thickness, coating continuity) and different batches of coating material may be avoided.

Test Example 3

The lorcaserin hydrochloride hemihydrate crystalline Form III prepared in preparation example 1 and the cocrystal in the present invention were compared in stability test for 10 days under conditions of high temperature and light exposure. The high temperature is 80° C., the lighting condition is 6000 lx illumination. Purities and the maximum individual impurity contents of samples before and after the stability test were detected by HPLC. The results were shown in Table 6.

TABLE 6

The stability testing under conditions of high temperature and light exposure

| Compounds | 0 day | | 10 days under conditions of high temperature and light exposure | | changed value | |
|---|---|---|---|---|---|---|
|  | HPLC purity (A %) | maximum individual impurity value (A %) | HPLC purity (A %) | The maximum individual impurity content (A %) | Decrease in HPLC purity (A %) | Increase in maximum individual impurity value (A %) |
| Lorcaserin hydrochloride hemihydrate crystalline Form III | 99.4 | 0.1 | 90.1 | 9.4 | 9.3 | 9.3 |

TABLE 6-continued

The stability testing under conditions of high temperature and light exposure

| Compounds | 0 day | | 10 days under conditions of high temperature and light exposure | | changed value | |
|---|---|---|---|---|---|---|
| | HPLC purity (A %) | maximum individual impurity value (A %) | HPLC purity (A %) | The maximum individual impurity content (A %) | Decrease in HPLC purity (A %) | Increase in maximum individual impurity value (A %) |
| Cocrystal in the present invention | Lorcaserin 67.5 Benzoic 32.0 acid | 0.1 | Lorcaserin 62.8 Benzoic 31.7 acid | 4.9 | Lorcaserin 4.7 Benzoic 0.3 acid | 4.8 |

The stability data shown in Table 6 indicated that, under conditions of high temperature and light exposure, the purity of lorcaserin hydrochloride hemihydrate crystalline Form III was decreased by 9.3%, its maximum individual impurity content was increased by 9.3%; while the purity of lorcaserin in the cocrystal of the present invention was decreased by 4.7%, benzoic acid in the cocrystal thereof was decreased by 0.3%, its maximum individual impurity was increased by 4.8%. Therefore, the stability of the cocrystal in present invention under conditions of high temperature and light exposure is much better than that of the known lorcaserin hydrochloride hemihydrate crystalline Form III.

The described above are only specific embodiments for illustrating the present invention, but without limiting it thereto. Any changes or alternations, without creative work, made by those skilled in the art within the technical scope disclosed by the present invention, should fall within the scope of the present invention.

What is claimed is:

1. Cocrystal of lorcaserin hydrochloride and benzoic acid with the structural formula shown below

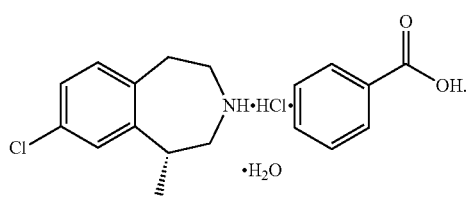

2. The cocrystal of lorcaserin hydrochloride and benzoic acid according to claim 1, wherein when measured using Cu-Kα radiation, the X-ray powder diffraction pattern of the cocrystal, expressed as 2θ angles, has the following characteristic peaks: 4.5±0.2°, 9.0±0.2°, 12.3±0.2°, 18.0±0.2°, 19.4±0.2° and 23.0±0.2°.

3. The cocrystal of lorcaserin hydrochloride and benzoic acid according to claim 2, wherein the X-ray powder diffraction pattern of the cocrystal, expressed as 2θ angles, has the following characteristic peaks: 4.5±0.2°, 9.0±0.2°, 11.7±0.2°, 12.3±0.2°, 13.5±0.2°, 16.9±0.2°, 18.0±0.2°, 19.4±0.2°, 20.4±0.2°, 22.6±0.2°, 23.0±0.2° and 23.5±0.2°.

4. The cocrystal of lorcaserin hydrochloride and benzoic acid according to claim 3, wherein the X-ray powder diffraction pattern of the cocrystal, expressed as 2θ angles, has the following characteristic peaks with their relative intensities:

| Diffraction angel 2θ | Relative intensity % |
|---|---|
| 4.5 ± 0.2° | 7.3 |
| 9.0 ± 0.2° | 53.9 |
| 11.7 ± 0.2° | 6.0 |
| 12.3 ± 0.2° | 6.9 |
| 13.5 ± 0.2° | 6.7 |
| 16.9 ± 0.2° | 7.9 |
| 18.0 ± 0.2° | 22.9 |
| 18.2 ± 0.2° | 16.0 |
| 19.4 ± 0.2° | 18.9 |
| 20.4 ± 0.2° | 11.4 |
| 22.6 ± 0.2° | 58.1 |
| 23.0 ± 0.2° | 100.0 |
| 23.5 ± 0.2° | 38.1 |
| 24.1 ± 0.2° | 28.4 |
| 25.7 ± 0.2° | 13.0 |
| 26.8 ± 0.2° | 16.5 |
| 28.0 ± 0.2° | 9.1 |
| 29.4 ± 0.2° | 11.9 |
| 30.9 ± 0.2° | 7.5. |

5. The cocrystal of lorcaserin hydrochloride and benzoic acid according to claim 1, wherein when measured at 100K in temperature, has the following single-crystal unit cell parameters: axial length: a=6.1734(6) Å, b=7.6376(5) Å, c=39.233(4) Å; dihedral angle: α=90°, β=90°, γ=90°; space group: P 1 1 2₁.

6. The cocrystal of lorcaserin hydrochloride and benzoic acid according to claim 2, wherein the Fourier transform infrared spectrum of the cocrystal has characteristic peaks at wave numbers of 3384, 2971, 2861, 2524, 2362, 1700, 1595, 1315, 1270, 1119, 946, 818 and 710 cm$^{-1}$.

7. A preparation method of the cocrystal of lorcaserin hydrochloride and benzoic acid according to claim 1, comprising:

(1) forming a solution of benzoic acid in an organic solvent, wherein the organic solvent is selected from the group consisting of alcohols, ketones and esters, adding lorcaserin hydrochloride hemihydrate, the molar ratio of lorcaserin hydrochloride hemihydrate to benzoic acid is from 1:1 to 1.5:1, after the adding step, stirring the mixture for crystallization, and obtaining the cocrystal; or (2) forming a solution of lorcaserin hydrochloride hemihydrate in an organic solvent, wherein the organic solvent is selected from the group consisting of alcohols, ketones and esters, adding benzoic acid to the solution, the molar ratio of lorcaserin hydrochloride hemihydrate to benzoic acid is from 1:1 to 1:3, after the adding step, stirring for crystallization, and obtaining the cocrystal; or (3) forming a mixed system of lorcaserin, hydrochloric acid and benzoic acid in an organic solvent, wherein the organic solvent is selected from the group consisting of alcohols, ketones, esters and halo alkanes, the molar ratio of lorcaserin, hydrochloric acid and benzoic acid is from 1:1:1 to 1:2:3, stirring the mixture for crystallization, and obtaining the cocrystal; or (4) adding a solvent to a mixture of lorcaserin hydrochloride hemihydrate and benzoic acid in which lorcaserin hydrochloride hemihydrate has an equal molar ratio to benzoic acid, keeping the mixture wetted completely with the solvent, grinding the mixture to dryness, and obtaining the cocrystal, wherein the solvent is selected from the group consisting of water and organic solvents.

8. A pharmaceutical composition comprising a therapeutically effective amount of the cocrystal of lorcaserin hydrochloride and benzoic acid according to claim 1, and at least one pharmaceutically acceptable carrier or additive.

9. The pharmaceutical composition according to claim 8, wherein the pharmaceutical composition is in the solid oral dosage form selected from the group consisting of tablets, capsules, granules, pills and powders.

10. A method of treating a disease associated with $5HT_{2C}$, comprising administering an effective amount of the cocrystal of lorcaserin hydrochloride and benzoic acid according to claim 1; wherein the disease associated with $5HT_{2C}$ is obesity.

11. The pharmaceutical composition according to claim 9, wherein the pharmaceutical composition is in a sustained-release or controlled-release solid oral dosage form.

12. The preparation method according to claim 7, wherein (1) the organic solvent is selected from the group consisting of $C_1$ to $C_4$ alcohols, ethyl acetate and acetone; (2) the organic solvent is selected from the group consisting of $C_1$ to $C_4$ alcohols, ethyl acetate and acetone; (3) the organic solvent is selected from the group consisting of $C_1$ to $C_4$ alcohols, ethyl acetate, acetone and dichloromethane; or (4) the solvent is selected from the group consisting of acetone, acetonitrile and water.

13. The preparation method according to claim 12, wherein the organic solvent in (1), (2) and (3) is isopropanol.

14. The preparation method according to claim 7, wherein (1) the concentration of the solution of benzoic acid in the organic solvent is from 75 to 120 mg/mL; (2) the concentration of the solution of lorcaserin hydrochloride hemihydrate in the organic solvent is from 50 to 100 mg/mL; (3) the weight volume ratio of lorcaserin to the organic solvent in the mixed system is from 100 mg:1 mL to 240 mg:1 mL; or (4) the weight volume ratio of the mixture to the solvent is from 150 mg:1 mL to 240 mg:1 mL.

15. The preparation method according to claim 7, wherein (1) lorcaserin hydrochloride hemihydrate is added in 2 to 6 equal parts, and the mixture is stirred for 10 to 15 minutes after each addition; or (2) benzoic acid is added in 2 to 6 equal parts, and the mixture is stirred for 10 to 15 minutes after each addition.

16. The preparation method according to claim 7, wherein the operation temperature of the preparation method is from 10° C. to 40° C.

17. The preparation method according to claim 7, wherein (1) the crystallization time is from 8 to 48 hours; (2) the crystallization time is from 8 to 48 hours; or (3) the crystallization time is from 10 to 24 hours.

* * * * *